United States Patent
Biglieri et al.

(10) Patent No.: US 6,958,577 B2
(45) Date of Patent: Oct. 25, 2005

(54) APPARATUS FOR IMAGING THE INNER PART OF A BODY, PARTICULARLY FOR DIAGNOSTIC IMAGING THEREOF

(75) Inventors: Eugenio Biglieri, Masio (IT); Osvaldo Pugliese, Genoa (IT); Lorenzo Bessi, Florence (IT); Luigi Satragno, Genoa (IT); Luciano Schiavini, Crema (IT)

(73) Assignee: Esaote, S.p.A., Monferrato (IT)

( * ) Notice: Subject to any disclaimer, the term of this patent is extended or adjusted under 35 U.S.C. 154(b) by 0 days.

(21) Appl. No.: 10/154,911

(22) Filed: May 28, 2002

(65) Prior Publication Data

US 2002/0183609 A1 Dec. 5, 2002

(30) Foreign Application Priority Data

May 24, 2001 (IT) .................................. SV2001A0017
Jun. 7, 2001 (IT) .................................. SV2001A0020

(51) Int. Cl.$^7$ .................................. G01V 3/00
(52) U.S. Cl. .................................. 314/318; 324/322
(58) Field of Search .................................. 324/318, 322, 324/300, 306, 307, 309, 312, 314

(56) References Cited

U.S. PATENT DOCUMENTS

| | | | |
|---|---|---|---|
| 4,543,959 A | | 10/1985 | Sepponen |
| 4,674,107 A | * | 6/1987 | Urban et al. .................. 378/98 |
| 4,926,456 A | * | 5/1990 | Bock et al. .................. 378/177 |
| 5,146,924 A | | 9/1992 | Sepponen |
| 5,525,905 A | * | 6/1996 | Mohapatra et al. .......... 324/318 |
| 5,568,050 A | | 10/1996 | Hennig |
| 5,572,567 A | | 11/1996 | Khutoryansky et al. |
| 5,666,055 A | * | 9/1997 | Jones et al. .................. 324/318 |
| 6,106,472 A | | 8/2000 | Chiang et al. |
| 6,138,495 A | | 10/2000 | Paltieli et al. |
| 6,210,333 B1 | | 4/2001 | Gardner et al. |
| 6,339,717 B1 | | 1/2002 | Baumgartl et al. |

FOREIGN PATENT DOCUMENTS

| | | |
|---|---|---|
| DE | 199 11 988 A1 | 9/2000 |
| EP | 0 355 042 A2 | 2/1990 |
| EP | 0 591 542 A1 | 4/1994 |
| EP | 0 774 670 A1 | 5/1997 |
| EP | 0 817 211 A1 | 1/1998 |
| EP | 1 004 269 A1 | 5/2000 |
| JP | 9-319516 | 12/1997 |
| JP | 2000-135212 | 5/2000 |
| JP | 2000-262511 | 9/2000 |
| JP | 2001-95777 | 4/2001 |
| JP | 2001-145629 | 5/2001 |
| WO | 96/32065 | 10/1996 |
| WO | 97/15840 A1 | 5/1997 |
| WO | 00/04493 A1 | 1/2000 |
| WO | 01/31358 A1 | 5/2001 |

* cited by examiner

*Primary Examiner*—Louis Arana
(74) *Attorney, Agent, or Firm*—Burns, Doane, Swecker & Mathis, L.L.P.

(57) ABSTRACT

An apparatus for imaging the inner part of a body, particularly for diagnostic imaging thereof, including at least means for imaging and displaying images according to at least one type of beams, waves or signals transmitted toward a body or a part thereof to be examined, the said means being means for generating at least one type of waves or beams which are transmitted toward the body or the part thereof to be internally imaged and means for receiving said type of waves or beams transmitted by the body under examination or by the part thereof or deriving from the excitation of said part or body under examination, from the reflection and/or transmission and/or modification of waves, of the beams transmitted against said body under examination or the part thereof.

26 Claims, 4 Drawing Sheets

APPARATUS FOR IMAGING THE INNER PART OF A BODY, PARTICULARLY FOR DIAGNOSTIC IMAGING THEREOF

This application claims priority under 35 U.S.C. §§ 119 and/or 365 to IT SV2001A00017 filed in Italy on 24 May 2001 and to SV2001A00020 filed in Italy on 07 June 2001; the entire contents of which are hereby incorporated by reference.

BACKGROUND OF THE INVENTION

1. Field of the Invention

The invention relates to an apparatus for imaging the internal part of a body, particularly for diagnostic imaging thereof. Particularly, the invention relates to an apparatus for imaging the internal part of a body, particularly for diagnostic imaging thereof, comprising at least means for generating at least one type of waves or beams which are transmitted toward the body or the part thereof to be internally imaged and means for receiving said type of waves or beams transmitted by the body under examination or by the part thereof or deriving from the excitation of said part or body under examination, from the reflection and/or transmission and/or modification of waves, of the beams transmitted against said body under examination or the part thereof, there being provided means for uniquely relating the information of the waves or beams retransmitted by the body under examination or the part thereof, to a space position of an image unit element (so-called pixel or voxel) and means for reconstructing the image from the array of pixels or voxels obtained thereby, which relate the information of the received waves or beams to brightness and/or color characteristics of the individual pixels.

2. Description of Related Art

Such apparatuses are well-known and include ultrasound imaging apparatuses, Nuclear Magnetic Resonance imaging apparatuses, X-Ray apparatuses, etc.

A particular kind of such medical examination devices, especially relating to nuclear magnetic resonance imaging devices, so called dedicated MRI devices are very interesting due to their low costs and their simple and cheap installation which do not give rise to problems as the one arising from a very high weight or the need of very large rooms which has also to be shielded against electromagnetic noise of the surrounding environment. Dedicated MRI devices are able to carry out imaging of limited body parts or anatomical districts and therefore often there is the need to have more than one device. Thus there is the need of further reducing their overall volume by effectively integrating the single parts forming this devices.

U.S. Pat. No. 6,339,717 deals with the hardware integration of MRI apparatuses by providing a hardware architecture which integrates a high amount of the hardware in a commercially available personal computer. U.S. Pat. No. 6,339,717 teaches to house the hardware of the apparatus in a dedicated console which is separated from the other parts of the apparatus. This has the drawback that a considerable amount of space is needed since the personal computer and at least the input devices and the monitor associated thereto needs a table or a furniture where the computer case and the said peripherals has to be placed.

OBJECTS AND SUMMARY

Nevertheless it is also possible to further integrate the structure of such devices in order to limit weight and overall volume.

The present invention aims provide an apparatus for imaging the internal part of a body which has a high level of structural integration ensuring at the same time to show a relatively friendly appearance for the patient and the maximum possible comfort for the person operating the device.

These aims have to be reached without increasing the costs of the apparatus and on the contrary by further limiting such costs.

Thanks to the fact that the hardware is housed inside the case or the frame of the case or a frame for housing and/or supporting the means for generating, transmitting and receiving the waves or beams, the additional furniture or cabinet for housing the hardware is no longer necessary.

Alternatively the hardware can be housed in the console for housing at least the command and control input means and the at least one monitor for displaying the image data.

Alternatively the hardware can also be housed at the patient supporting element, such as a patient chair, a table/chair, a table, or the like in the structure or frame thereof.

According to the preferred embodiment the hardware is housed partially or completely in the case or the frame for housing and/or supporting the means for generating, transmitting and receiving the waves or beams and/or partially or completely at the patient supporting element, such as a patient chair, a table/chair, a table, or the like in the structure or frame thereof and/or partially or completely in a console for housing the command and control input means and the at least one monitor for displaying the image data.

According to a further improvement, the console for housing the command and control input means and the at least one monitor for displaying the image data is supported by the case or the frame for housing and/or supporting the means for generating, transmitting and receiving the waves or beams or by the patient supporting element, such as a patient chair, a table/chair, a table, or the like by the structure or frame thereof by means of a combination of articulated levers which allow the console to be moved in one or more directions.

The console is designed having a form similar to a lap-top computer or a notebook computer, since the hardware is housed in the structure of the patient supporting means or of the case or frame of the means for generating, transmitting and receiving the waves or beams.

The high integration of the hardware also permits one to integrate in the same frames or cases for the means for generating, transmitting and receiving the waves or beams, and in the same console for the command and control input means and the at least one monitor for displaying the image data the hardware and the peripheral control units for two different kinds of medical examination devices such as a nuclear magnetic resonance imaging device and an ultrasound imaging device. Obviously other kinds of medical examination devices might be considered in place of the nuclear magnetic resonance imaging device or of the ultrasound imaging device.

Further medical examining devices might be integrated in the same structure.

The dependent claims deals with further improvements and embodiments of the present invention.

BRIEF DESCRIPTION OF THE DRAWINGS

The features of the present invention and the advantages deriving there from will appear more clearly from the following description of preferred embodiments illustrated in the annexed drawings in which.

DETAILED DESCRIPTION OF THE PREFERRED EMBODIMENTS

Figure 1:
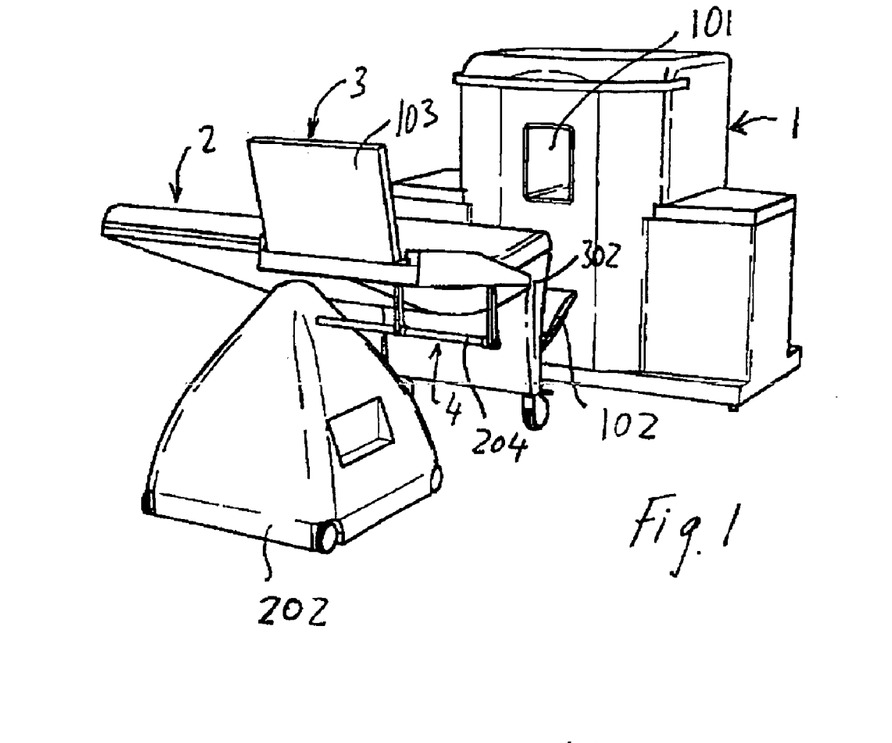
FIGS. 1 and 2 are two perspective views, in two different directions, and with the table in different orientations, of an integrated imaging apparatus according to the invention.
Figure 2:
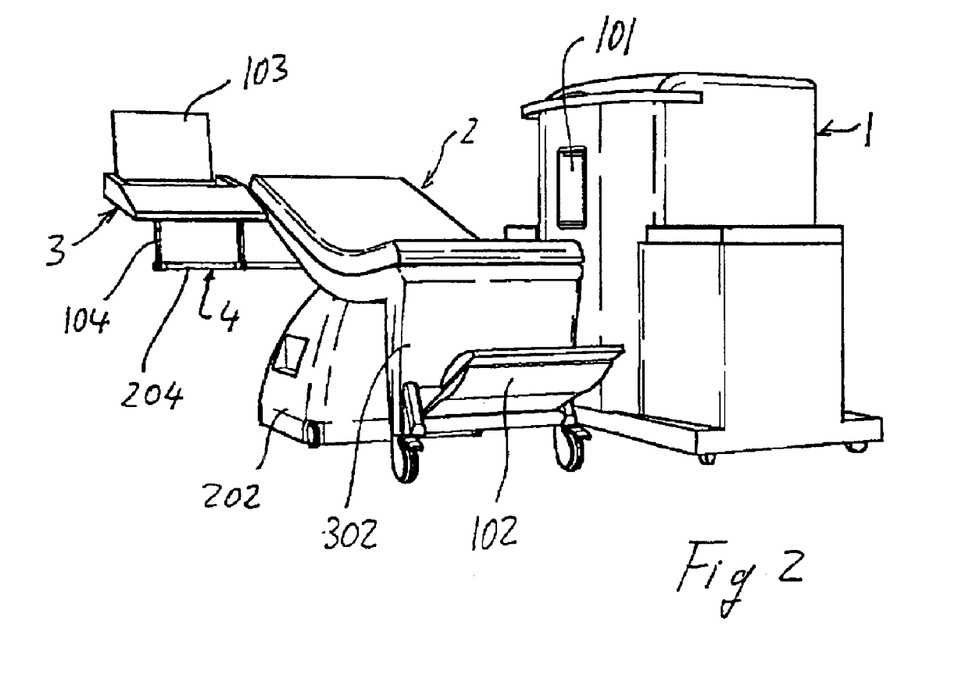

FIGS. 1 and 2 show an integrated apparatus for imaging, particularly a Nuclear Magnetic Resonance imaging apparatus or such an apparatus integrated with an ultrasound imaging apparatus. The Nuclear Magnetic Resonance imaging device comprises a magnetic structure generally denoted as 1, which includes a permanent, resistive or superconducting magnet for generating a static field in a cavity 101 designed to receive a part of the patient body; coils for transmitting radio-frequency pulses for exciting nuclear spins, gradient coils for applying selecting and phase and frequency encoding gradients and receiving coils. All these elements are known per se and are not shown in detail.

In FIGS. 1 and 2, the magnetic structure 1 is contained in a separate case and has a peripherally closed annular shape, with two opposite open sides. The case including the magnetic structure 1 has two lateral extensions 201 which form a cabinet-like enclosure in the form of a shielded electrical cabinet for housing at least a part or all of the processing electronics.

The electronics may comprise (with reference now to the Nuclear Magnetic Resonance imaging device, the latter generally comprises, besides the magnetic structure 1) circuits for generating the excitation sequences and for capturing images and circuits for receiving nuclear spin echoes, which contain the information, i.e. the data for image reconstruction, as well as circuits for reconstructing images, i.e. for extracting image data from received signals and for relating said data to the space location wherefrom it is transmitted, hence to an image pixel. Further, the device comprises circuits for controlling and setting the modes of the Nuclear Magnetic Resonance imaging device, and circuits for processing, display and storage of reconstructed images.

A patient table 2, in the form of a table/chair is associated to the magnetic structure 1. Particularly, the table is shorter than the patient body and, in the portion associated to the lower limbs, substantially reaches the knee level, but is able to extend beyond it by a footrest element 102 which may be displaced to various positions, for instance to a lowered and tilted position parallel to the ground with a footrest function, or to a lowered and vertically tilted position against the end side of the table or even to a position in which it extends and completes the surface of the table. A detailed construction example of a table of this type is provided in the published patent application EP 913 122.

Particularly, the table is mounted on an intermediate carriage which consists of a cabinet-like element 202. At one of its end sides, particularly the one associated to the lower limbs, the table has a vertical leg 302, also in the form of a carriage, which extends substantially all along the table, thereby having the function of a pair of traditional legs.

A control console 3 is associated to the patient table 2, particularly but without limitation to the end opposite to the one associated to the lower limbs.

The control console 3 has an upper surface with the different ultrasound imaging controls and advantageously an ultra-slim display 103, e.g. a liquid crystal display, which is articulated to the console 3 in such a manner as to allow it to be tilted to a lifted operating position and to a rest position in which it lays over the upper face of the console 3.

The control console 3 is secured to a support structure 4 formed by swinging arms 104 and supporting and sliding beams 204, in such a manner that it can be displaced relative to the vertical level, swung forward and rearward, and translated transverse to the longitudinal axis of the table 2.

These displacements may be obtained by using any support structure construction, depending on the structure and on the aspect of the table. In the embodiment as shown in the Figures, and with particular reference to FIGS. 3 to 5, the support structure 4 of the console 3 has at least one transverse support guide 204 for transverse sliding, for example extending telescopically or as a rod sliding in slide supports, whereon at least two swinging arms 104 are mounted, which are spaced in the axial direction of the guide 204, and are articulated by their opposite ends to the case of the console 3. The guide 204 may be secured to the lower side of the table 2 by one or more additional vertical and/or longitudinal guides (with reference to the longitudinal axis of the table) and/or with rotary joints according to a vertical axis. The two arms 104 may themselves be secured to the console case 3 to pivot about it with the interposition of a rotary joint for the rotation of the console 3 with respect to a vertical axis. Also, the guide 204 may slide in the transverse direction to such an extent as to allow the console to slide independently on one side or the other of the table 2. As an alternative to the illustrated means, the console may be supported by a jointed arm which may have one or more successive arm sections, connected to each other by spherical or cardan joints, and is fastened to the structure of the table. The jointed arm may be fabricated as is known, for instance for display supporting arms, or the like, with the appropriate changes required by the conditions of displacement of the console 3 relative to the table 2. Advantageously, both the illustrated structure 3 and the possibly provided jointed arm have cavities wherein the wires for connecting the console 3 to other electronic units associated to the imaging devices may pass and be housed.

Figure 3:
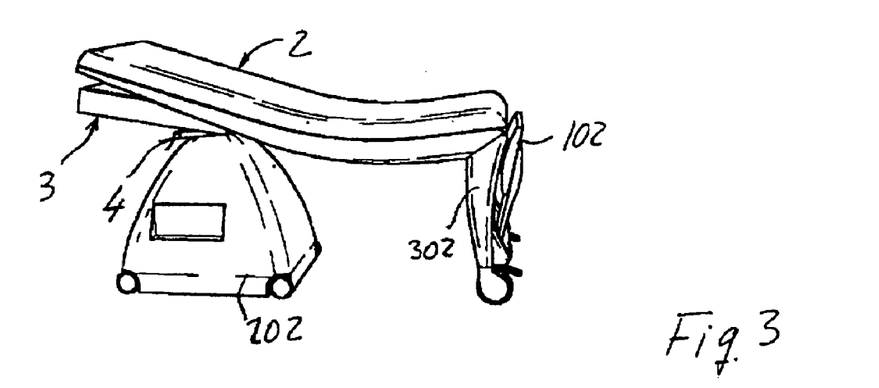
FIGS. 3 to 5 are different perspective views of the apparatus as shown in FIG. 1, in which the magnetic structure of the Nuclear Magnetic Resonance imaging device is omitted, and the console is shown in different operating and rest positions.
Figures 4, 5:
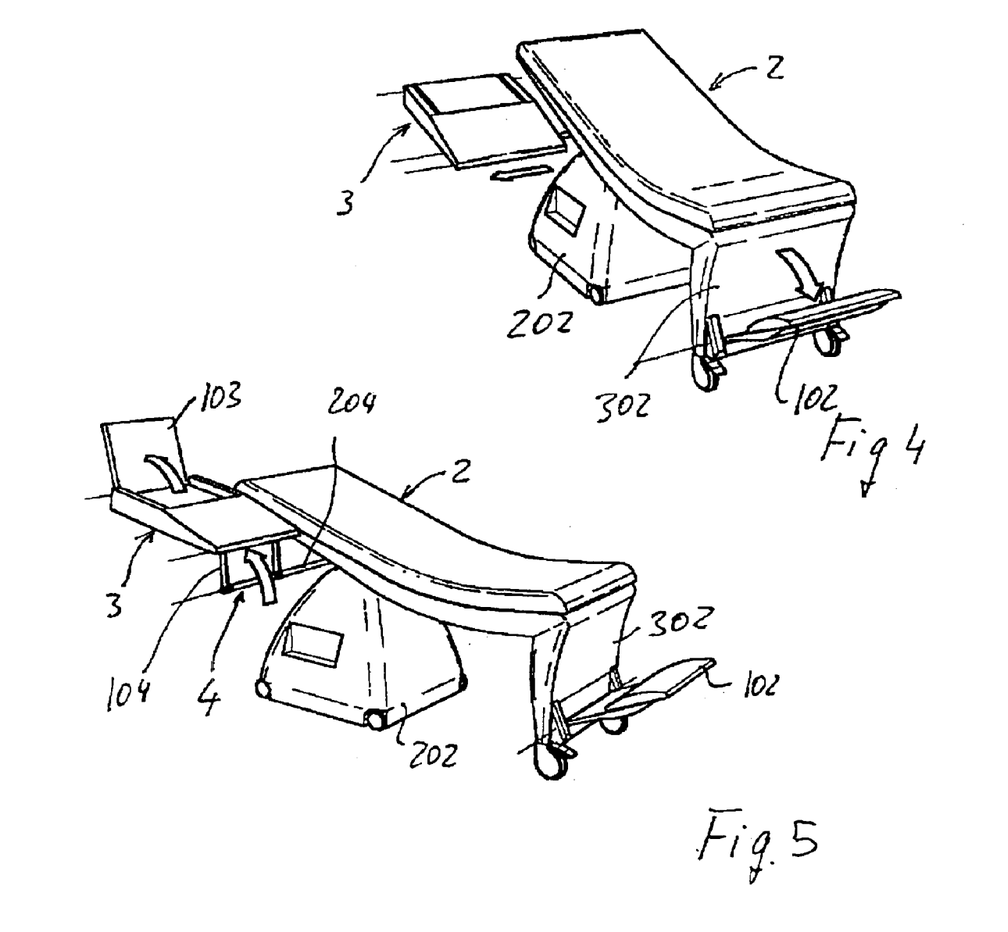

Thanks to the above construction, the console 3 may be displaced to any position relative to the table 2. Particularly, there are provided an operating position adjacent to one of the sides of the table 2 and a rest position, in which, after tilting the display into the rest position, against the upper surface of the console, the latter may be completely displaced under the surface of the table.

Thanks to this construction, besides ensuring the highest operational convenience, the retractable position of the console within the size of the table allows to reduce the damaging risks, for instance, while displacing the console, and to prevent any hindrance to the freedom of movement of the personnel when intervening on the patient.

Here, in order to maintain a relatively limited size of the console 3, the cabinet-like base 202 of the table 2 is provided in the form of an electrical cabinet for housing at least a part or all of the processing electronics of at least part of the circuits for generating the excitation sequences and for capturing images and circuits for receiving nuclear spin echoes, which contain the information, i.e. the data for image reconstruction, as well as circuits for reconstructing images, i.e. for extracting image data from received signals and for relating said data to the space location wherefrom it is transmitted, hence to an image pixel. Further, the device comprises, like the ultrasound imaging device, circuits for controlling and setting the modes of the Nuclear Magnetic Resonance imaging device, and circuits for processing, display and storage of reconstructed images.

According to an advantageous embodiment, the electronics is appropriately divided between the console 3 and the cabinet-like base 202 of the table 2 and the extensions 201 of the case of the magnetic structure All the electronic circuits distributed in the console 3, in the cabinet like base 202 of the table 2 and in the lateral extensions 201 of the case of the magnetic structure 1 are connected together by communication lines which are preferably electro magnetically shielded in order not to generate interference.

Figure 6:
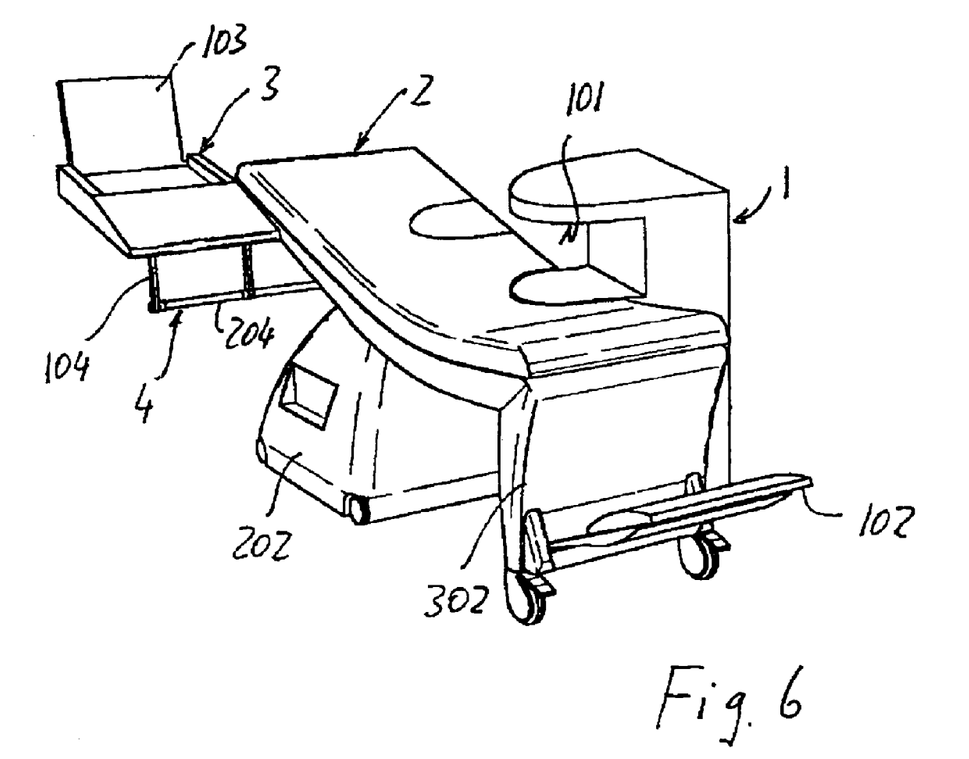
FIG. 6 shows a variant embodiment of the integrated apparatus as shown in FIGS. 1 to 5, in which the magnetic structure is very small and has an inverted U or C shape.

According to a further embodiment of FIG. 6, a magnetic structure may be provided which is displaced relative to the patient table, hence to the body under examination or the part thereof to a predetermined extent and in predetermined directions.

In this case, the magnetic structure 1 or the patient table 2, or both may be displaced relative to each other.

Figures 7, 8:
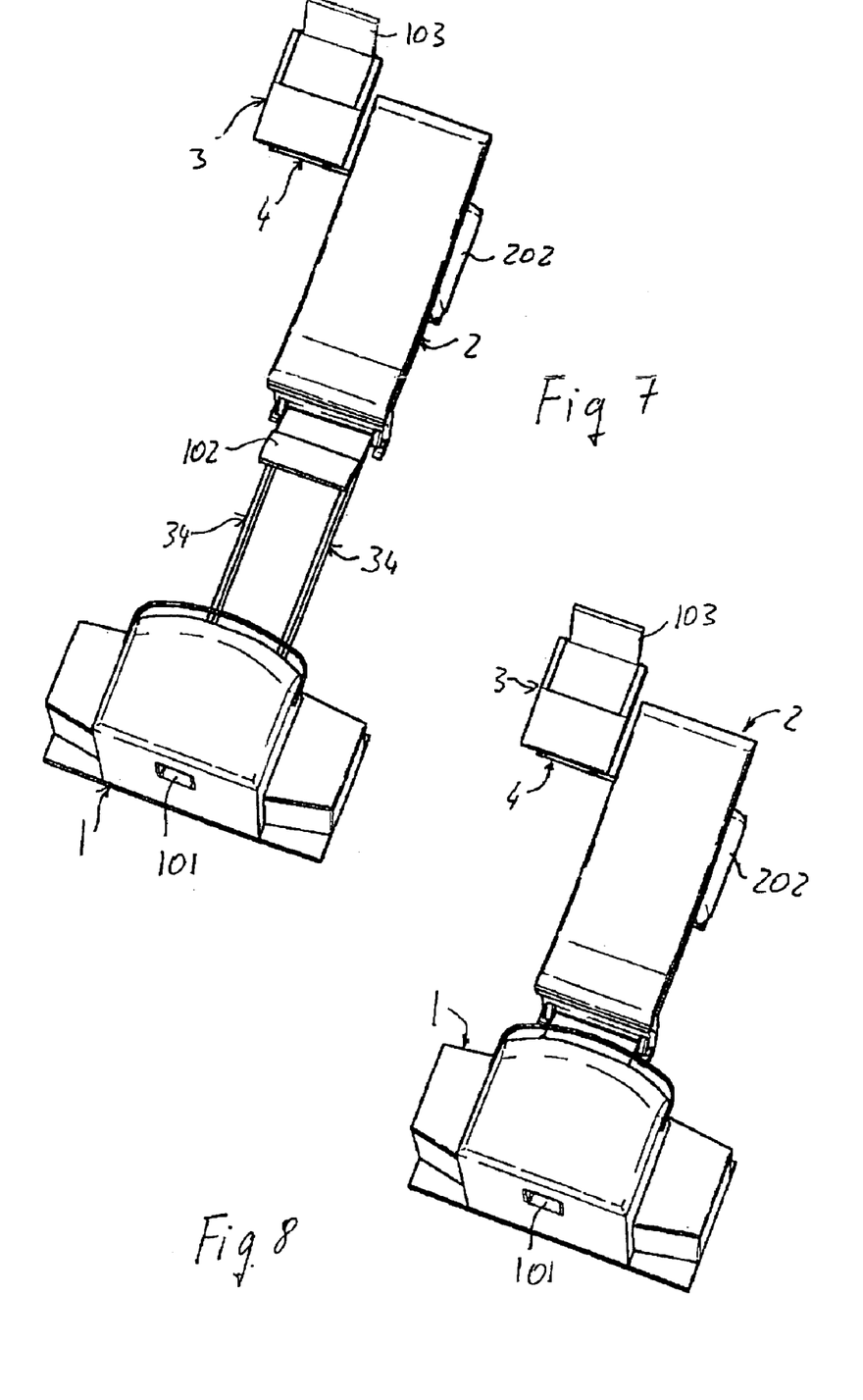
FIGS. 7 and 8 show a variant of the integrated apparatus, in which the magnetic structure of the Nuclear Magnetic Resonance imaging device is mounted with the table on a common guide for a controlled and measurable relative displacement.

In the embodiment of FIGS. 7 and 8, there is provided at least one guide 34 on which the table 2 and/or the magnetic structure 1 and/or both are mounted to be displaced on slides or carriages.

Furthermore, the table 2 and/or the magnetic structure 1 and/or both may be arranged to rotate at least about a vertical axis.

Position locating means may be provided which determine the relative position of the table 2, i.e. the patient and the magnetic structure 1.

In FIG. 6, the magnetic structure has a C or u shape and is much smaller than the table, a surface of the said magnetic structure being shaped in such a way as to form displaceable inserts which complete the table 2. More recesses might be provided in the table which are opened on one longitudinal side thereof and which are shaped correspondingly to the horizontal pole of the magnetic structure. For closing the recess which is not used or completed by the magnetic structure a complementary insert is provided.

The magnetic structure as well as the table may be mounted on carriages and may be displaceable freely or by means of guides one with respect to the other.

As it might appear clearly from the above description, providing several cabinet like premises in the structure of the case of the magnetic structure 1 and in the structure or frame of the table provides a lot of space for housing the hardware needed for driving the apparatus and for processing the image data in order to display the images. This fact does not only permit a command input console with integrated display which is very small and has a lap-top or notebook computer like shape and/or dimension but allows also to have space for housing further hardware for integrating in the same device a further different imaging apparatus for example an ultrasound imaging apparatus.

In this condition the hardware specifically designed for the nuclear magnetic resonance imaging device may be housed in the extensions 201 of the case of the magnetic structure, while the hardware of the ultrasound imaging device may be housed in the cabinet-like base 202 of the table 2.

Particularly, the base 202 contains the typical electronic circuits, specifically dedicated to the control of the ultrasonic probe for the transmission of ultrasonic waves, focusing thereof and reception of reflected waves, the reconstruction according to the focusing rule and the processing of received signals as regards the extraction of data useful for imaging and correlation thereof to a precise space position and to a precise and unique pixel of the image to be displayed. Moreover, these circuits may also comprise all the sections for filtering and for processing the data extracted from the received signals with various processing modes, such as those known as B-Mode, Harmonic Imaging, Doppler, Color Doppler and other data processing and extraction modes. When devices for detecting other data or physiological parameters, e.g. an electrocardiogram are provided, the cabinet 202 may also contain the control and processing units of these devices and possibly the units for synchronizing the signal of the electrocardiogram or other devices, for instance with the electronics of the ultrasound imaging device, such as in the apparatuses known as "stress ultrasound imaging" or the like.

On the other hand, besides the command input devices and the images display monitor for the nuclear magnetic resonance imaging device, the console 3 includes the electronic circuits for controlling and setting the ultrasound imaging modes, the circuits for image processing and controlling the display means and the means for setting the display and detection controls also for the ultrasound imaging device, such as the selection of imaging modes, amongst the modes mentioned above (B-Mode, Harmonic Imaging, Doppler, Color Doppler, and other data processing and extraction methods).

Advantageously, according to a preferred embodiment, the dedicated circuits of the ultrasound imaging system in the cabinet 202 and those of the nuclear magnetic resonance imaging device in the extensions 201 of the magnetic structure case 1 communicate with the console 3 via communication interfaces which encode the data to be exchanged between the console 3 and the dedicated control and processing circuits contained in the cabinets with a common structure, for instance a so-called bidirectional communication bus.

Mass storage means may be also associated to the console 3 or the cabinet 202, such as hard disks, or the like, means for reading or writing removable data storage media, such as floppy disks, CR-Rom, CD-R, CD-RW and/or flashcard memories or the like, and/or other output peripherals, such as printers and/or other data entry peripherals, such as scanners or the like.

Advantageously, the console 3 has a microprocessor unit, the functions thereof being implemented in software form.

This structure may be easily used to also integrate, in the apparatus of the invention, a program for processing, storage and centralized control of the diagnostic data of the patient, obtained either through the specific analyses performable by the integrated apparatus or through other apparatuses, which may be entered in the patient diagnostic data control program through the various data entry means as mentioned above.

According to a possible alternative embodiment, two separate consoles (not shown in detail) may be provided each one dedicated only to the nuclear magnetic imaging device and to the ultrasound imaging device. Nevertheless, by using the same circuit configuration as the ultrasound imaging device, the specific part for controlling the magnetic structure and the associated units like excitation coils, gradient coils, etc., and the specific part designed to receive echo signals, to reconstruct and extract image data and relate it to a specific pixel of an array of image pixels, may be housed wholly or partly in the case of the magnetic structure 1 whereas the image processing means are housed wholly or partly in the cabinet 202 since this hardware section may show several identical units as the ones needed for processing ultrasound image data and thus may be shared between the nuclear magnetic resonance imaging device and the ultrasound imaging device.

Here, the processing and control electronics of the Nuclear Magnetic Resonance imaging device should be provided with a communication interface, i.e. a bidirectional bus for communication with the console 3, which is of the same type as the one used for the control and processing electronics of the ultrasound imaging device.

By this arrangement, the means for image processing and display control may be the same as used in the ultrasound imaging device.

Mass storage means, data entry means, like scanners or the like, for entering data detected by other separate devices and/or data transmission means, like printers or the like may also be shared by the two types of devices.

If the ultrasound imaging device also comprises an ECG unit, the latter may be also interfaced with the Nuclear Magnetic Resonance imaging device, like the ultrasound imaging device, through means for synchronizing resonance imaging with the physiological parameters detected by the ECG.

According to an additional characteristic, the console 3 may have image processing means which combine images of the same section obtained by the ultrasound imaging device and by the Nuclear Magnetic Resonance imaging device. In this case, the advantage consists in the possibility to mutually combine the information of the image obtained by ultrasound imaging and that obtained by Nuclear Magnetic Resonance imaging. Besides obtaining better and more complete results, this combination option may allow to use imaging modes of a reduced duration and complexity for both devices, since even the characteristics that are hardly visible through an imaging method may be visible through the other imaging method.

The combination may be simply obtained by displaying the two images obtained each with one of the two imaging methods sequentially or side by side, or by overlaying the two images, or even by a real combination and mutual integration of the image data obtained by the two imaging modes.

Since the simultaneous use of the two imaging methods may cause adverse effects on one of the two imaging modes, e.g. the presence of ultrasonic transducer power may generate noise which cause the formation of artifacts in the Nuclear Magnetic Resonance imaging signals, the two devices are arranged to be operated in fast alternate succession, on a time-sharing basis. To this end, the console 3 has means for entering time sharing parameters, and a control unit is provided which, based on said parameters, controls the alternate operation of said two imaging devices.

Nevertheless, the two modes may be also used in combination, for instance with the help of contrast agents which are caused to burst or be destroyed by the power provided by the ultrasonic probe, whereas imaging is performed by Nuclear Magnetic Resonance in these conditions of the contrast agents.

Possibly, the table structure 2 may integrate the control and dedicated processing circuits signals of devices for detecting further physiological parameters, such as ECG, EMG, EGG, and the circuits for synchronizing the ultrasound imaging and Nuclear Magnetic Resonance imaging processes with said parameters.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An MRI or ultrasound apparatus for imaging a part of a body, comprising:

means for generating at least one type of waves or beams which are transmitted toward the part of the body to be imaged and means for receiving said type of waves or beams transmitted by the part of the body or deriving from the excitation of said part of the body, from the reflection or transmission or modification of the waves or the beams transmitted to said part of the body;

a controlling electronic circuit for controlling the generating means and the receiving means;

processing electronic circuits for processing the received beams or waves from the part of the body and transforming the received signals into displayable image data;

a command and control input device;

at least one monitor for displaying the image data;

a frame for housing or supporting the generating means and the receiving means;

a console for housing at least the command and control input device and the at least one monitor for displaying the image data;

wherein at least a part of the processing electronic circuits is housed in the frame and at least some of the electronic circuits are housed in the console; and a communication line connecting the electronic circuits housed in the frame with the electronic circuits housed in the console.

2. The apparatus as claimed in claim 1, wherein the apparatus further comprises a patient supporting element and the part of the electronics is housed in the patient supporting element.

3. The apparatus according to claim 2, wherein the console is in the form of a lap top computer case or of a notebook computer and is supported by articulated means at the patient supporting element.

4. The apparatus according to claim 2, wherein the table, chair or table/chair has at least one cabinet-like base block element for housing, at least partly, the frame.

5. The apparatus as claimed in claim 4, wherein the at least one cabinet-like base block element includes at least a median support member in the form of a three-dimensional pedestal, enclosing a space for housing, at least partly, the frame.

6. The apparatus according to claim 2, wherein the frame is housed completely in the frame or in the patient supporting element, or in the console.

7. The apparatus as claimed in claim 2, wherein the apparatus includes a Nuclear Magnetic Resonance imaging and displaying device and an ultrasound imaging and displaying device integrated in the same apparatus.

8. The apparatus as claimed in claim 7, wherein the command and control input device and the at least one monitor for displaying the image data of the nuclear magnetic resonance imaging device and of the ultrasound imaging device are housed in a common console or in separated individual consoles for each imaging device.

9. The apparatus according to claim 7, wherein the command and control input device and the at least one monitor for displaying the image data of the nuclear magnetic resonance imaging device and of the ultrasound imaging device are housed in separated individual consoles for each imaging device, the consoles being placed each on one side of the chair or patient supporting table.

10. The apparatus as claimed in claim 7, wherein the command and control input device and the at least one monitor for displaying the image data of the nuclear magnetic resonance imaging device and of the ultrasound imaging device are housed in a common console, the common console comprising means for entering specific commands for each type of imaging devices, which means are separated for each of the specific imaging device or shared by all imaging devices.

11. The apparatus as claimed in claim 2, wherein apparatus includes a Nuclear Magnetic Resonance imaging device and a magnetic structure of the nuclear magnetic resonance imaging device is connected to the patient supporting element with guides and carriages which are linked to the magnetic structure and to the patient supporting element.

12. The apparatus as claimed in claim 11, wherein tracer means are provided for locating a relative position between the patient supporting element and the magnetic structure.

13. An apparatus as claimed in claim 11, wherein the magnetic structure and the patient supporting element are freely displaced relative to each other, there being provided a tracer or sensor means.

14. The apparatus according to claim 1, wherein the frame is electro-magnetically shielded.

15. The apparatus according to claim 1, further comprising a communication line provided between the controlling electronic circuit and the processing electronic circuits.

16. The apparatus according to claim 1, wherein the part of the electronic circuits is housed in parts of the frame which have patient supporting functions.

17. The apparatus as claimed in claim 1, wherein the apparatus includes a Nuclear Magnetic Resonance imaging and displaying device or an ultrasound imaging and displaying device.

18. The apparatus as claimed in claim 1, wherein the patient supporting element includes a patient chair, a table/chair, or a table.

19. An MRI or ultrasound apparatus for imaging a part of a body, comprising:

means for generating at least one type of waves or beams which are transmitted toward the part of the body to be imaged and means for receiving said type of waves or beams transmitted by the part of the body or deriving from the excitation of said part of the body, from the reflection or transmission or modification of the waves or the beams transmitted to said part of the body;

an electronic circuit for controlling the generating means and the receiving means;

an electronic circuit for processing the received beams or waves from the part of the body and transforming the received signals into displayable image data;

a command and control input device;

at least one monitor for displaying the image data;

a frame for housing or supporting the generating means and the receiving means;

a console for housing at least the command and control input device and the at least one monitor for displaying the image data;

wherein a part of the electronic circuits is housed in the frame and a remainder of the electronic circuits is housed in the console; and a communication line connecting the electronic circuits housed in the frame with the electronic circuits housed in the console;

wherein the console is in the form of a lap top computer case or of a notebook computer and is supported by articulated means at the frame.

20. An MRI or ultrasound apparatus for imaging a part of a body, comprising:

means for generating at least one type of waves or beams which are transmitted toward the part of the body to be imaged and means for receiving said type of waves or beams transmitted by the part of the body or deriving from the excitation of said part of the body, from the reflection or transmission or modification of the waves or the beams transmitted to said part of the body;

an electronic circuit for controlling the generating means and the receiving means;

an electronic circuit for processing the received beams or waves from the part of the body and transforming the received signals into displayable image data;

a command and control input device;

at least one monitor for displaying the image data;

a frame for housing or supporting the generating means and the receiving means;

a console for housing at least the command and control input device and the at least one monitor for displaying the image data;

wherein a part of the electronic circuits is housed in the frame and a remainder of the electronic circuits is housed in the console; and a communication line connecting the electronic circuits housed in the frame with the electronic circuits housed in the console;

wherein the apparatus further comprises a patient supporting element and part of the electronics is housed in the patient supporting element;

wherein the console is directly supported by a table, chair or table/chair, via articulated or jointed means.

21. The apparatus as claimed in claim 20, wherein the console is supported by one or more jointed arms or by a combination of swinging beams and arms or levers, which are jointed to each other in such a manner as to allow different degrees of freedom of motion in the vertical direction, transverse to the longitudinal axis of the table, chair or table/chair or a swinging motion about a horizontal axis or about a vertical axis.

22. The apparatus as claimed in claim 20, wherein the console is supported by a slide which runs on horizontal means, transverse to the longitudinal axis of the table, chair or table/chair whereto it is articulated in such a manner as to be movable angularly about an axis parallel to said guide, via at least one pair of swinging arms, whereby said console may be swung between a level above the supporting surface or another part of the table, chair or table/chair and a level below said supporting surface or said other part of the chair or table or table/chair, and even translated transverse to the longitudinal axis of the table to a position in which it is adjacent thereto, and at least retracted in such a manner as to essentially disappear under the surface or a portion of the chair, table or table/chair.

23. The apparatus as claimed in claim 22, wherein the transverse slide extends to such an extent relative to the table, chair and/or table/chair whereby the console may be translated from an adjacent position on one side to an adjacent position on the opposite side.

24. The apparatus as claimed in claim 20, wherein the console is supported by at least one swinging arm on the chair, table and/or table/chair, which arm is articulated via a spherical joint connection, to the console and/or to the table, chair or table/chair.

25. The apparatus as claimed in claim 24, wherein the arm is arranged to be jointed or to consist of two or more articulated sections.

26. An MRI or ultrasound apparatus for imaging a part of a body, comprising:

a table for supporting a patient and a base for supporting the table;

means for generating at least one type of waves or beams which are transmitted toward the part of the body to be imaged and means for receiving said type of waves or beams transmitted by the part of the body or deriving from the excitation of said part of the body, from the reflection or transmission or modification of the waves or the beams transmitted to said part of the body;

a controlling electronic circuit for controlling the generating means and the receiving means;

processing electronic circuits for processing the received beams or waves from the part of the body and transforming the received signals into displayable image data;

a command and control input device;

at least one monitor for displaying the image data;

a frame for housing or supporting the generating means and the receiving means;

a console for housing at least the command and control input device and the at least one monitor for displaying the image data;

wherein at least a part of the processing electronic circuits is housed in the base that supports the table; and a communication line connecting the electronic circuits housed in the base with the remaining electronic circuits.

* * * * *

UNITED STATES PATENT AND TRADEMARK OFFICE
CERTIFICATE OF CORRECTION

PATENT NO. : 6,958,577 B2
DATED : October 25, 2005
INVENTOR(S) : Eugenio Biglieri et al.

It is certified that error appears in the above-identified patent and that said Letters Patent is hereby corrected as shown below:

<u>Title page,</u>
Item [30], Foreign Application Priority Data,
change "May 24, 2001" to -- May 28, 2001 --; and change "June 7, 2001" to -- June 8, 2001 --.

Signed and Sealed this

Seventh Day of February, 2006

JON W. DUDAS
*Director of the United States Patent and Trademark Office*